US005114605A

United States Patent [19]

Mizui et al.

[11] Patent Number: 5,114,605

[45] Date of Patent: May 19, 1992

[54] LUBRICANT OIL FOR REFRIGERATORS

[75] Inventors: Kinya Mizui, Ichihara; Yoshiaki Furuya, Chiyoda, both of Japan

[73] Assignee: Mitsui Petrochemical Industries, Ltd., Tokyo, Japan

[21] Appl. No.: 605,273

[22] Filed: Oct. 30, 1990

[30] Foreign Application Priority Data

Nov. 2, 1989 [JP] Japan ........................ 1-286645

[51] Int. Cl.[5] ........................ C09K 5/04; C07C 69/00; C10M 107/26

[52] U.S. Cl. ........................ 252/68; 252/52 A; 252/56 R

[58] Field of Search ........................ 558/266, 265, 276; 252/68, 52 A, 56 R

[56] References Cited

U.S. PATENT DOCUMENTS

| | | | |
|---|---|---|---|
| 2,379,252 | 6/1945 | Muskat et al. | 558/266 |
| 2,387,934 | 10/1945 | Muskat et al. | 558/266 |
| 3,632,828 | 1/1972 | Frevel et al. | 558/276 |
| 3,657,310 | 4/1972 | Fevel | 558/276 |
| 3,725,455 | 4/1973 | D'Angelo et al. | 558/266 |
| 4,072,704 | 2/1978 | Langdon | 558/266 |
| 4,217,298 | 8/1980 | Shikata et al. | 558/265 |
| 4,755,316 | 7/1988 | Magid et al. | 252/68 |
| 4,948,525 | 8/1990 | Sasaki et al. | 252/52 A |

FOREIGN PATENT DOCUMENTS

| | | |
|---|---|---|
| 63395 | 4/1982 | Japan . |
| 182337 | 7/1988 | Japan . |

*Primary Examiner*—Prince Willis, Jr.
*Assistant Examiner*—J. Silbermann
*Attorney, Agent, or Firm*—Sherman and Shalloway

[57] ABSTRACT

A lubricant oil for refrigerators, industrial gears, automotive engines, automotive gear oil, fibers and as a rolling lubricant oil, comprising a glycol ether carbonate represented by the general formula [I]

$$R_1-O-(R_3-O)_m CO-(OR_4)_n OR_2 \quad [I]$$

wherein $R_1$ and $R_2$ are each independently an aliphatic group, an alicyclic group, an aromatic group and an aromatic-substituted aliphatic group each having not greater than 20 carbon atoms, $R_3$ and $R_4$ are each independently an ethylene group or an isopropylene group, and m and n are each independently an integer of 2 to 100, and optionally containing ozone layer-nondestructive Freon such as Freon R-134a.

1 Claim, No Drawings

LUBRICANT OIL FOR REFRIGERATORS

FIELD OF THE INVENTION

The present invention relates to a lubricant oil composition, more particularly to a lubricant oil composition used for industrial gear oil, automotive engine oil, automotive gear oil, lubricant oil for fibers, lubricant oil for rolling and lubricant oil for refrigerators, which are excellent in lubricating properties and detergency. The present invention relates still more particularly to a lubricant oil composition most adapted as a lubricant oil for refrigerators where hydrofluorocarbons (HFC) such as Freon R-134a which when nondestructive to the ozone layer is used as a refrigerant.

BACKGROUND OF THE INVENTION

Lubricant oils include industrial gear oil, engine oil, lubricant oil for fibers, lubricant oii for rolling and lubricant oil for refrigerators.

As the working conditions for various industrial machines become severe recently, industrial gear oil has come to be required to maintain its lubricating properties and detergency at high temperature. In particular, improved lubricating properties and detergency have come to be required of the industrial gear oil used in the processes for thermosetting coating or baking food. There have heretofore been used lubricant oils of a synthetic hydrocarbon type, a carboxylic acid ester type or a glycol type.

Synthetic hydrocarbon oil and carboxylic acid ester oil, however, are still insufficient in lubricating properties, and, in addition, they have such a drawback that they cannot be used as lubricant oil at high temperature because they form carbide when heated over a long period of time. On the other hand, though glycol lubricant oil is advantageous in that it does not form much carbide when heated over a long period of time, it has insufficient lubricating properties and high hygroscopicity. Accordingly, improvement thereof has been desired.

Engine oil has been required to have lubricating properties and dispersancy at higher temperature over a longer period to cope with improved performance of automotive engines. When addition of the additives for the engine oil is attempted to respond to such a requirement, it results in an increase in the additives. The increase in the amount of additive induces harmful results such as precipitation or deposition of mayonnaise sludge. Though there has heretofore been tried the use of mineral oil in combination with synthetic hydrocarbon oil or carboxylic acid ester oil, the resultant base oil shows both insufficient lubricating properties and dispersancy when used at high temperature over a long period of time. Lubricant oil for 2-cycle engines, different from that for the above-mentioned automobile engines, that is, 4-cycle engines, is burnt after it is added to gasoline due to the mechanism of the engines, and therefore its detergency is especially important. Though castor oil, polybutene and the like have been used as lubricant oil for 2-cycle engines, both their lubricating properties and detergency are insufficient.

Gear oil for automobiles, especially for ATF is required to have a low friction coefficient and decreased change thereof with the lapse of time. Antifriction agents and friction-adjusting agents have therefore been used. Automotive gear oil containing these additives has a problem that the friction coefficient thereof increases with time.

As a lubricant oil for fibers, carboxylic acid ester lubricant oil and glycol lubricant oil have usually been employed, but they cannot simultaneously satisfy lubricating properties and detergency.

Lubricant oil containing tallow as its main ingredient has been conventionally used as rolling lubricant oil. In spite of its highly lubricating properties and excellent rolling efficiency, such lubricant oil is extremely poor in detergency, and hence it requires a process for washing the remaining tallow. Though carboxylic acid ester lubricant oil has been used as rolling lubricant oil, it shows little practicality due to poor lubricating properties, despite its significantly excellent detergency.

With the alteration of a refrigerant gas for refrigerators to Freon R-134a ($CH_2F$-$CF_3$) which is an ozone layer-nondestructive HFC, mineral oil and alkylbenzenes, which heretofore have been used for lubricant oil for refrigerators, have come not to be used therefore because they have no mutual solubility with the refrigerant gas. Glycol ether type lubricant oil has currently been developed for the lubricant oil for refrigerators where the above-mentioned refrigerant is used.

For example, U.S. Pat. No. 4,755,316 discloses a compression refrigerator composition composed of tetrafluoroethane and a polyoxyalkylene glycol having a molecular weight of 300 to 2,000 and a kinematic viscosity at 37° C. of about 25 to 150 cSt.

Such glycol ether lubricant oil, however, generally has insufficient thermal stability and high hygroscopicity, and in addition it has been pointed out that the glycol ether lubricant oil has such a drawback that it shrinks rubber sealing materials such as nitrile rubber (NBR) and increases their hardness.

U.S. Pat. No. 3,627,810 discloses a process for preparing carbonates of higher alcohols represented by the formula R'OCOOR", and the carbonates are described to be useful as hydraulic oil, lubricant oil and plasticizers. The specification, however, does not clearly describe their concrete use, for example, for lubricant oil for refrigerators, especially refrigerator lubricant oil excellent in mutual solubility with ozone layer-nondestructive Freon. In the above formula, R' and R" are each a higher alcohol residue.

U.S. Pat. No. 3,657,310 discloses a process for preparing carbonates represented by the formula ROCOO-$(AO)_nR'$. Though these carbonates are described to be useful as lubricant oil, hydraulic oil and plasticizers, their concrete use, for example, for lubricant oil for refrigerators, especially refrigerator lubricant oil excellent in mutual solubility with ozone layer-nondestructive Freon. In the above-mentioned formula, R and R' each denote a monovalent aliphatic group, and A indicates an alkylene group having 2 to 4 carbon atoms, with n denoting an integer of not less than 1.

European Patent No. 089,709 discloses a process for preparing a carbonate of a higher alcohol by ester interchange reaction between a higher alcohol having a molecular weight of 100 to 270 and an alcohol carbonate having a low boiling point, and a lubricant oil composition containing such a carbonate of a higher alcohol.

Japanese Patent L-O-P No. 37,568/1973 discloses a motor transmitting liquid containing at least one carbonate represented by the general formula $$R^1O\text{-}(X\text{—}OCOO)_n\text{-}X\text{—}OR^2$$

wherein $R^1$ and $R^2$ are each independently hydrogen, an aliphatic group, an aromatic-substituted aliphatic group, an aromatic group, an acyl group, an alkoxycarbonyl group or an aryloxy group, n is a number of 1 to 10, and X is an alkylene group having at least two carbon atoms in the main molecular carbon chain, the molecular chain optionally containing a cycloalkylene group, an aralkylene group, an arylene group or at least one hetero atom. The use of the carbonate esters disclosed in the publication, however, are for transmitting liquid and not for lubricant oil.

Furthermore, Japanese Patent Publication No. 4727/1971 discloses a process for preparing polyethylene glycol monomethyl ether carbonates represented by the general formula $$CH_3\text{-}(OCH_2CH_2)_x\text{-}OCOO\text{-}(CH_2CH_2O)_y\text{-}CH_3$$

wherein x and y are each 2 or 3.

The publication teaches that the polyethylene glycol monomethyl ether carbonates described above are useful for the preparation of a brake liquid, and they are also useful as synthetic lubricants. However, it does not clearly describe concrete use, for example, lubricant oil for refrigerators, especially refrigerator lubricant oil excellent in mutual solubility with ozone layer-nondestructive Freon.

The present invention is intended to solve the above-described problems involved in the prior art method, and an object of this invention is to provide a lubricant oil composition having excellent lubricating properties and detergency, and also having excellent mutual solubility with ozone layer-nondestructive Freon such as Freon R-134a.

SUMMARY OF THE INVENTION

The lubricant oil composition according to the present invention comprises a glycol ether carbonate represented by the general formula [I]

$$R_1\text{—}O\text{-}(R_3\text{—}O)_m\text{-}CO\text{-}(OR_4)_n\text{-}OR_2 \qquad [I]$$

wherein $R_1$ and $R_2$ are each independently a member selected from the group consisting of an aliphatic group, an alicyclic group, an aromatic group and an aromatic-substituted aliphatic group each having not greater than 20 carbon atoms, $R_3$ and $R_4$ are each independently an ethylene group or an isopropylene group, and m and n are each independently an integer of 2 to 100.

The lubricant oil composition according to this invention has excellent lubricating properties and detergency, and its viscosity at low temperature can be easily decreased compared with mineral oil or ester lubricant oil. As a result, the lubricant oil composition according to this invention can be widely used for industrial gear oil, automotive engine oil, automotive gear oil, lubricant oil for refrigerators, lubricant oil for fibers and rolling lubricant oil.

The lubricant oil composition according to this invention is excellent not only in the above-described properties but also in mutual solubility with ozone layer-nondestructive Freon such as Freon R-134a, and therefore they can be used as lubricant oil for refrigerators where ozone layer-nondestructive Freon such as Freon R-134a is employed as a refrigerant.

In the lubricant oil composition of this invention, there can also be used, as lubricant oil for refrigerators, the one containing ozone layer-nondestructive Freon such as R-134a in addition to a glycol ether carbonate represented by the general formula [I] described above.

The term "lubricant oil composition" in this specification includes lubricant oil comprising a glycol ether carbonate of this invention and other ingredients, and lubricant oil composed of only said glycol ether carbonate.

DETAILED DESCRIPTION OF THE INVENTION

The lubricant oil composition of the present invention is concretely illustrated hereinafter.

The lubricant oil composition according to the present invention comprises a glycol ether carbonate represented by the general formula [I]

$$R_1\text{—}O\text{-}(R_3\text{—}O)_m\text{-}CO\text{-}(OR_4)_n\text{-}OR_2 \qquad [I]$$

$R_1$ and $R_2$ are each independently a member selected from the group consisting of an aliphatic group, an alicyclic group, an aromatic group and an aromatic-substituted aliphatic group each having not greater than 20 carbon atoms.

Here, concrete examples of an aliphatic hydrocarbon group represented by $R_1$ and $R_2$ include methyl, ethyl, propyl, isopropyl, isobutyl, sec-butyl, tert-butyl, pentyl, isopentyl, neopentyl, n-hexyl, isohexyl, n-heptyl, isoheptyl, n-octyl, isooctyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, isohexadecyl, n-heptadecyl, isoheptadecyl, n-octadecyl, isooctadecyl, n-nonyldecyl, isononyldecyl, n-eicosanyl and isoeicosanyl.

Concrete examples of an alicyclic hydrocarbon group represented by $R_1$ and $R_2$ include cyclohexyl, 1-cyclohexenyl, methylcyclohexyl, dimethylcyclohexyl, decahydronaphtyl and tricyclodecanyl.

Furthermore, concrete examples of an aromatic hydrocarbon group represented by $R_1$ and $R_2$ include phenyl, o-tolyl, p-tolyl, m-tolyl, 2,4-xylyl, mesityl and 1-naphtyl.

Still furthermore, concrete examples of an aromatic-substituted aliphatic hydrocarbon group represented by $R_1$ and $R_2$ include benzyl, methylbenzyl, β-phenylethyl (phenethyl), 1-phenylethyl, 1-methyl-1-phenylethyl, p-methylbenzyl, styryl and cinnamyl.

In the above-described general formula [I], $R_3$ and $R_4$ are each independently an ethylene group or an isopropylene group.

Moreover, in the general formula [I] described above, m and n are each independently an integer of 2 to 100.

In the present invention, $R_1$, $R_2$, $R_3$, $R_4$, m and n in the above general formula [I] are selected in accordance with the use. For example, when $R_1$, $R_2$, $R_3$, $R_4$, m and n for the glycol ether carbonate represented by the general formula [I] are selected in such a manner that the resultant glycol ether carbonate has a kinematic viscosity (JIS K-2283) of about 8 cSt at 100° C., a lubricant oil composition containing the resultant glycol ether carbonate described above is preferably used for lubricant oil for refrigerators where ozone layer-nondestructive Freon such as Freon R-134a is employed as a refrigerant. The preferred use of the above-mentioned glycol ether carbonate is due to its especially excellent mutual solubility with ozone layer-nondestructive Freon at temperatures as low as −20° C. and as high as 90° C.

Glycol ether carbonates represented by the general formula [I] described above can be prepared, for example, by ester interchange reaction of a polyalkylene glycol monoalkyl ether in the presence of an excessive amount of a carbonate of an alcohol having a relatively low boiling point. Such a process does not require the use of a highly toxic gas, as is the case with the phosgene process, and is therefore preferable from the standpoint of safety.

Concrete examples of polyalkylene glycol monoalkyl ethers described above include ethylene glycol monoalkyl ethers, diethylene glycol monoalkyl ethers, triethylene glycol monoalkyl ethers, tetraethylene glycol monoalkyl ethers, propylene glycol monoalkyl ethers, dipropylene glycol monoalkyl ethers, tripropylene glycol monoalkyl ethers and tetrapropylene glycol monoalkyl ethers. Moreover, in the present invention, polyalkylene glycol monoalkyl ethers formed as by-products during the manufacture of the polyalkylene glycol monoalkyl ethers mentioned above and having relatively high boiling points may also be singly used in place thereof, and they may also be used in a mixture with the polyalkylene glycol monoalkyl ethers mentioned above.

Furthermore, a glycol ether carbonate represented by the general formula [I] having a viscosity appropriate for desired use may be prepared by suitably selecting the length of the hydrocarbon group and the polymerization degree of the polyalkylene glycol. Moreover, characteristics such as the low temperature characteristics, heat resistance and rubber swelling properties of the polyalkylene glycol can be freely adjusted by selecting the structure of the hydrocarbon group and polyalkylene glycol group thereof.

The thus obtained glycol ether carbonates have excellent lubricating properties, low hygroscopicity and good detergency compared with glycol ethers, and therefore they can be used for industrial gear oil, automotive engine oil, automotive gear oil, lubricant oil for fibers, lubricant oil for rolling and lubricant oil for refrigerators.

The lubricant oil composition according to the present invention comprises a glycol ether carbonate in an amount of 1 to 100 parts by weight based on 100 parts by weight of the total lubricant oil composition. As a result, the glycol ether carbonate can be used solely as lubricant oil, and it can also be used in combination with other components to form lubricant oil.

For example, in the case of using the lubricant oil composition of this invention as industrial gear oil, automotive engine oil and automotive gear oil, the lubricant oil composition may be combined with such usable components in addition to the glycol ether carbonate as mineral oil, for example, neutral oil and bright stock. It may also be combined with an α-olefin oligomer such as liquid polybutene and liquid decene oligomer, a carboxylic acid ester such as di-isooctyl adipate, di-isooctyl sebacate and dilauryl sebacate, and vegetable oil. In this invention, the lubricant oil composition may also comprise such known additives for lubricant oil, which are described in a book entitled "Additives for Petroleum Products" edited by Toshio Sakurai (published in 1974 by Saiwai Shobo) and the like, as dispersants for cleaning, antioxidants, load-resistant additives, oiliness improvers and pour point depressants so long as the incorporation of the additives does not impair the object of the invention.

Furthermore, in the case of using the lubricant oil composition of this invention as lubricant oil for refrigerators, the lubricant oil composition may be combined with other usable components including glycol ethers and mineral oil such as neutral oil and bright stock in addition to the glycol ether carbonate. It may also be combined with an α-olefin oligomer such as liquid polybutene and liquid decene oligomer, a carboxylic acid ester such as di-isooctyl adipate, di-isooctyl sebacate and dilauryl sebacate, and vegetable oil. In the case of using the lubricant oil composition of the invention as lubricant oil for refrigerators where HFC such as Freon R-134a (tetrafluoroethane) is specifically employed as a refrigerant gas nondestructive to the ozone layer, other usable additives are limited to glycol ethers and carboxyic acid esters from the standpoint of the mutual solubility. The addition amount of these additives, however, is required to be less than 60% by weight of the entire lubricant oil composition from the standpoint of not deteriorating heat resistance, mutual solubility with Freon R-134a and hygroscopicity resistance. Moreover, the lubricant oil composition may contain known lubricant oil additives as described above. Furthermore, the lubricant oil composition for refrigerators may also contain ozone layer-nondestructive Freon such as Freon R-134a.

When there is used a glycol ether carbonate, which the lubricant oil composition of the present invention comprises, for lubricant oil for rolling, machining oil, lubricant oil for fibers, etc., the glycol ether carbonate may be used in an aqueous emulsion prepared with a suitable emulsifier as conventionally practiced.

EFFECT OF THE INVENTION

The lubricant oil composition according to this invention comprises a specific glycol ether carbonate, and therefore it has excellent lubricating properties and detergency. In addition, its viscosity at low temperature can be easily decreased compared with mineral oil or ester lubricant oil.

As a result, the lubricant oil composition according to this invention can be widely used for industrial gear oil, automotive engine oil, automotive gear oil, lubricant oil for refrigerators, lubricant oil for fibers and rolling lubricant oil.

The lubricant oil composition according to this invention is excellent not only in the above-described properties but also in mutual solubility with ozone layer-nondestructive Freon including Freon R-134a, and therefore it can be used as lubricant oil for refrigerators where ozone layer-nondestructive Freon such as Freon R-134a is employed as a refrigerant.

Concrete effects obtained when lubricant oil composition according to this invention is used as the above-mentioned lubricant oils are described below.

(1) Industrial gear oil

The lubricant oil composition of this invention can be used not only as general industrial gear oil but also as chain oil of which particularly excellent detergency and lubricating properties are required.

(2) Automotive engine oil

The lubricant oil composition of this invention is excellent in lubricating properties and detergency, and accordingly it can meet the recent requirement of highly improved properties for engine oil of which detergency is considered important.

The additives such as cleaning-dispersants and stabilizers for the lubricant oil composition of this invention can be reduced in amounts to be added compared with those used in the conventional automotive engine oil, and therefore there can be overcome problems such as mayonnaise sludge formation and precipitation of insoluble components, which are presumably caused by excessive use of these additives.

Furthermore, since the lubricant oil composition of this invention is excellent in both lubricating properties and detergency compared with the conventional lubricant oil for two-cycle engines, it can also be used as engine oil for two-cycle engines in addition to four-cycle engines.

(3) Automotive gear oil

The lubricant oil composition of this invention is excellent in lubricating properties and detergency, and in addition it has a friction coefficient which is low and changes little with the lapse of time.

(4) Lubricant oil for refrigerators

Since the lubricant oil composition of this invention comprises a specific glycol ether carbonate, it is soluble in Freon R-134a ($CH_2F-CF_3$) which is a HFC nondestructive to the ozone layer and when used as a refrigerant gas, has excellent thermal stability and hygroscopicity resistance, and it prevents shrinkage of rubber sealing materials such as NBR to maintain sealing effects. In addition, the lubricant oil composition of the invention can also maintain similar sealing effects for EPDM and SBR, and accordingly EPDM and SBR can be employed as rubber sealing materials.

(5) Lubricant oil for fibers

The lubricant oil composition of the invention has excellent lubricating properties and fuming-resistant properties compared with the conventional glycol ether lubricant oil.

(6) Rolling lubricant oil

The lubricant oil composition of this invention has lubricating properties and rolling ability equal to or more excellent than those of the conventional rolling lubricant oil containing mainly tallow, is volatilized without carbonization by only heating, and it is excellent in detergency. Accordingly, cleaning processes can be omitted after the lubricant oil composition is used. The present invention is illustrated below with reference to examples, but it should be construed that the invention is in no way limited to those examples.

Test procedures described below were applied to perform evaluation of properties of lubricant oil in Examples and Comparative Examples.

(1) Evaluation methods a. Kinematic viscosity by JIS K-2283 b. Viscosity at low temperature by ASTM D 2983 c. Friction characteristics

Friction coefficients of sample materials were measured under the following conditions by using a friction tester (trade name of SRV, manufactured by Optimol K.K.):

load: 200 N;

temperature: 50° C.;

period of time: 10 min;

amplitude: 1 mm;

number of vibration: 50 Hz; and test pieces: a disc in combination with a sphere, both made of SUJ-2.

The depth of the resultant wear defect was determined by measuring the defect depth of the disc after test using a surface roughness meter (trade name of Surfcom 200B, manufactured by Tokyo Seimitsu K.K.).

d. Thermal stability

A 20-g sample is placed in a 100 ml beaker, and the beaker is heated at 100° C. for 6.5 hours in an oven. The thermal stability thereof is evaluated from an (amount of sample weight decrease)/(initial sample weight) ratio. The sample has better thermal stability when it shows a smaller change (decrease) ratio.

e. Detergency

A 1-g sample is placed in a lid 5 cm in diameter of a container for ointment, and heated at 230° C. for 48 hours or 300° C. for 6 hours. In the case where the sample remains, it is black and solidified (in a carbonized state). The weight of the sample before and after the test is measured, and a remaining ratio of the sample is defined as a sludge formation ratio, from which detergency of the sample is evaluated.

f. Hygroscopicity

A 100 ml beaker is charged with a 30-g sample, and allowed to stand still for 48 hours in an air-conditioning bath kept at a temperature of 25° C. and relative humidity of 75%. The water concentration of the sample before and after the test is measured by Karl Fischer's method.

g. Rubber swelling properties

A flask containing a 20-ml sample is charged with 2 kinds of O-rings (P-22), that is, a nitrile rubber O-ring (JIS B 24011 B) and a fluororubber O-ring (JIS B 2401 4D), equipped with a condenser, and immersed in an oil bath at 120° C. for 70 hours. The two O-rings are taken out from the flask after the test, freed from the sample by wiping sufficiently, and the weight change of the O-rings is measured.

h. Mutual solubility with Freon R-134a

A test tube having an inner diameter of 10 mm and height of 20 cm is charged with a 1 ml sample, and Freon R-134a is slowly introduced into the test tube in an amount slightly larger than that of the sample from a bomb container while the test tube is being cooled in a dry ice-acetone bath. Then, the content is stirred with a spatula, and the test tube is transferred to a cooling bath at −20° C. The solubility of the sample is observed when the volume ratio of sample/(Freon R-134a) becomes 1/1. The mutual solubility is designated as O (mark) when the mixture becomes completely uniform, and it is designated as X (mark) when complete dissolution of the mixture is not observed.

EXAMPLE 1

A 5 liter 3 neck round bottom flask with a 10-plate Oldershow type distillation column and a thermometer was charged with 821 g (5 mols) of triethylene glycol monomethyl ether, 1351 g (15 mols) of dimethyl carbonate and 9 g of a methanol solution containing 30% by weight of $NaOCH_3$ (0.05 mol as $NaOCH_3$). The mixture was refluxed by heating in an oil bath with stirring under a nitrogen ambient atmosphere to react. Resultant methanol was distilled off 5 hours after the initiation of the reaction, and the reaction was continued until the internal temperature of the round bottom flask reached 130° C.

The reaction was continued while resultant methanol and dimethyl carbonate were being distilled off by connecting the round bottom flask to an evacuating apparatus and stepwise increasing evacuation degree of the ambient pressure. The reaction was terminated at the stage when the ambient pressure and the internal temperature of the round bottom flask reached 15 mmHg and 135° C., respectively.

The reaction solution was neutralized by introducing 2.9 g of an aqueous solution containing 85% by weight of phosphoric acid into the round bottom flask. Resultant precipitated salt was filtered out. The filtrate was distilled at wall temperature of 205° to 220° C. of the round bottom flask and under a reduced pressure of 1.7 mmHg by using a thin film distillation apparatus, and a low boiling point component was distilled off. The removed low boiling point component was in an amount of 25% by weight based on the entire reaction solution.

A high boiling point component of the reaction solution remaining in the round bottom flask was distilled off at a wall temperature of 260° C. under a reduced pressure of 0.15 mmHg. The removed high boiling point component was in an amount of 15% by weight based on the entire remaining reaction solution.

Bis{2-[2-(2-methoxyethoxy)ethoxy]ethyl} carbonate in an amount of 567 g was obtained by removing a low boiling point component and a high boiling point component from the reaction solution as described above.

Bis{2-[2-(2-methoxyethoxy)ethoxy]ethyl} carbonate was thus obtained in purity of 98.5% and in a yield of 64%.

The fundamental properties as a lubricant oil of the thus obtained carbonate are evaluated, and the results are shown in Table 1.

EXAMPLE 2

The reaction conducted in Example 1 was repeated except that 1,031 g of triethylene glycol monobutyl ether was used in place of triethylene glycol monomethyl ether.

The procedure of Example 1 was repeated at a wall temperature of 220° C. and under a reduced pressure of 1.5 mmHg to remove a low boiling point component from the reaction solution. A high boiling component was also removed by repeating the procedure of Example 1 at a wall temperature of 260° C. and under a reduced pressure of 0.2 mmHg. Bis{2-[2-(2-butoxyethoxy)ethoxy]ethyl} carbonate was thus obtained in an amount of 614 g.

Bis{2-[2-(2-butoxyethoxy)ethoxy]ethyl} carbonate was thus obtained in purity of 98.0% and in a yield of 56%.

The fundamental properties as a lubricant oil of the thus obtained carbonate are evaluated, and the results are shown in Table 1.

COMPARATIVE EXAMPLE 1

A propylene oxide type glycol ether ($\overline{M}n$ of 1520, $\overline{M}w\overline{M}n$ of 1.1) was similarly evaluated as lubricant oil.

Evaluation results of the fundamental properties thereof as lubricant oil are shown in Table 1.

COMPARATIVE EXAMPLE 2

Similar evaluation was conducted on lubricant oil (trade name of Suniso 331, prepared by Nihon Sun Sekiyu K.K.) for refrigerators where currently used Freon R-12 was employed. Evaluation results of the fundamental properties thereof as lubricant oil are shown in Table 1.

The lubricant oil is not mutually soluble with Freon R-134a which is nondestructive to the ozone layer.

TABLE 1

| | Ex. 1 | Ex. 2 | Comp. Ex. 1 | Comp. Ex. 2 |
|---|---|---|---|---|
| Viscosity characteristics | | | | |
| 100° C. Kinematic viscosity [cSt] | 2.77 | 3.21 | 10.6 | 6.0 |
| 40° C. Kinematic viscosity [cSt] | 10.21 | 11.86 | 55.8 | 54.9 |
| −20° C. Viscosity [poise] | 9.9 | 3.6 | 40 | 160 |
| Friction characteristics | | | | |
| Friction coefficient | 0.11 | 0.11 | 0.13 | 0.22 |
| Wear depth [μm] | 0.6 | 0.4 | 2.8 | 1.2 |
| Thermal stability (wt. change) [%] | −6.3 | −3.5 | −6.5 | −10.5 |
| Detergency | | | | |
| 230° C., 48 hrs | 0.2 | 0.4 | 4.9 | 15.1 |
| 300° C., 6 hrs | <0.1 | <0.1 | 2.2 | 5.0 |
| Hygroscopicity (Water content %) | | | | |
| Initial | 0.09 | 0.05 | 0.08 | 0.006 |
| After test | 0.16 | 0.10 | 2.45 | 0.007 |
| Rubber swelling properties (Wt. change) [%] | | | | |
| Nitrile rubber | +17.0 | +24.2 | −1.5 | +2.6 |
| Fluororubber | +9.6 | +2.2 | +0.4 | +0.3 |
| Mutual solubility*1 with Freon R-134a | | | | X |

*1: With mutual solubility
X: Without mutual solubility

What is claimed:

1. A lubricant oil for refrigerators, comprising (1) an ozone layer nondestructive hydrofluorocarbon (2) a sufficient amount to provide lubrication for said hydrofluorocarbon of a glycol ether carbonate represented by the general formula [I]

$$R_1-O-(R_3-O)_m-CO-(O-R_4)_n-OR_2 \qquad [I]$$

wherein $R_1$ and $R_2$ are each independently an aliphatic group, an alicyclic group, an aromatic group and an aromatic-substituted aliphatic group each having not greater than 20 carbon atoms, $R_3$ and $R_4$ are each independently an ethylene group or an isopropylene group, and m and n are each independently an integer of 2 to 100, and (3) residual ingredient which is at least any one of the group consisting of mineral oil and α-olefin oligomer.

* * * * *